(12) United States Patent
Marashdeh et al.

(10) Patent No.: US 9,791,396 B2
(45) Date of Patent: Oct. 17, 2017

(54) SPACE ADAPTIVE RECONSTRUCTION TECHNIQUE FOR ADAPTIVE ELECTRICAL CAPACITANCE VOLUME TOMOGRAPHY

(71) Applicants: Tech4Imaging LLC, Columbus, OH (US); Ohio State Innovation Foundation, Columbus, OH (US)

(72) Inventors: Qussai Marashdeh, Columbus, OH (US); Fernando Teixeira, Columbus, OH (US); Burak Gurlek, Columbus, OH (US); Zeeshan Zeeshan, Columbus, OH (US)

(73) Assignees: TECH4IMAGING LLC, Columbus, OH (US); OHIO STATE INNOVATION FOUNDATION, Columbus, OH (US)

( * ) Notice: Subject to any disclaimer, the term of this patent is extended or adjusted under 35 U.S.C. 154(b) by 253 days.

(21) Appl. No.: 14/706,614

(22) Filed: May 7, 2015

(65) Prior Publication Data
US 2016/0327503 A1 Nov. 10, 2016

(51) Int. Cl.
*G01N 27/22* (2006.01)
*G06T 11/00* (2006.01)
*A61B 5/053* (2006.01)

(52) U.S. Cl.
CPC .......... *G01N 27/226* (2013.01); *G06T 11/006* (2013.01); *A61B 5/0536* (2013.01)

(58) Field of Classification Search
None
See application file for complete search history.

(56) References Cited

U.S. PATENT DOCUMENTS

| 8,614,707 B2 | 12/2013 | Warsito |
| 2013/0085365 A1 | 4/2013 | Marashdeh |

OTHER PUBLICATIONS

Warsito et al, "Neural network multi-criteria optimization image reconstruction technique (NN-MOIRT) for linear and non-linear process tomography", Chemical Engineering and Processing: Process Intensification, vol. 42, Issues 8-9, Aug.-Sep. 2003, pp. 663-674 (Published 2003).*

* cited by examiner

*Primary Examiner* — Melissa Koval
*Assistant Examiner* — Felicia Farrow
(74) *Attorney, Agent, or Firm* — Standley Law Group LLP

(57) ABSTRACT

A capacitance system having a capacitance sensor provides a high resolution Spatial-Adaptive Reconstruction Technique (SART) for use with Adaptive Electrical Capacitance Volume Tomography (AECVT). The system is adapted to analyze information provided by an image reconstruction of a first spatial region of an imaging domain of the sensor; provide control signals to the sensor to increase the resolution at a second spatial region of the imaging domain of the sensor based on the prior image reconstruction of the first spatial region; obtain image reconstruction information for the second spatial region of the imaging domain; and combine the image reconstruction information for the first spatial region and the second spatial region to obtain a combined image of the imaging domain.

16 Claims, 10 Drawing Sheets

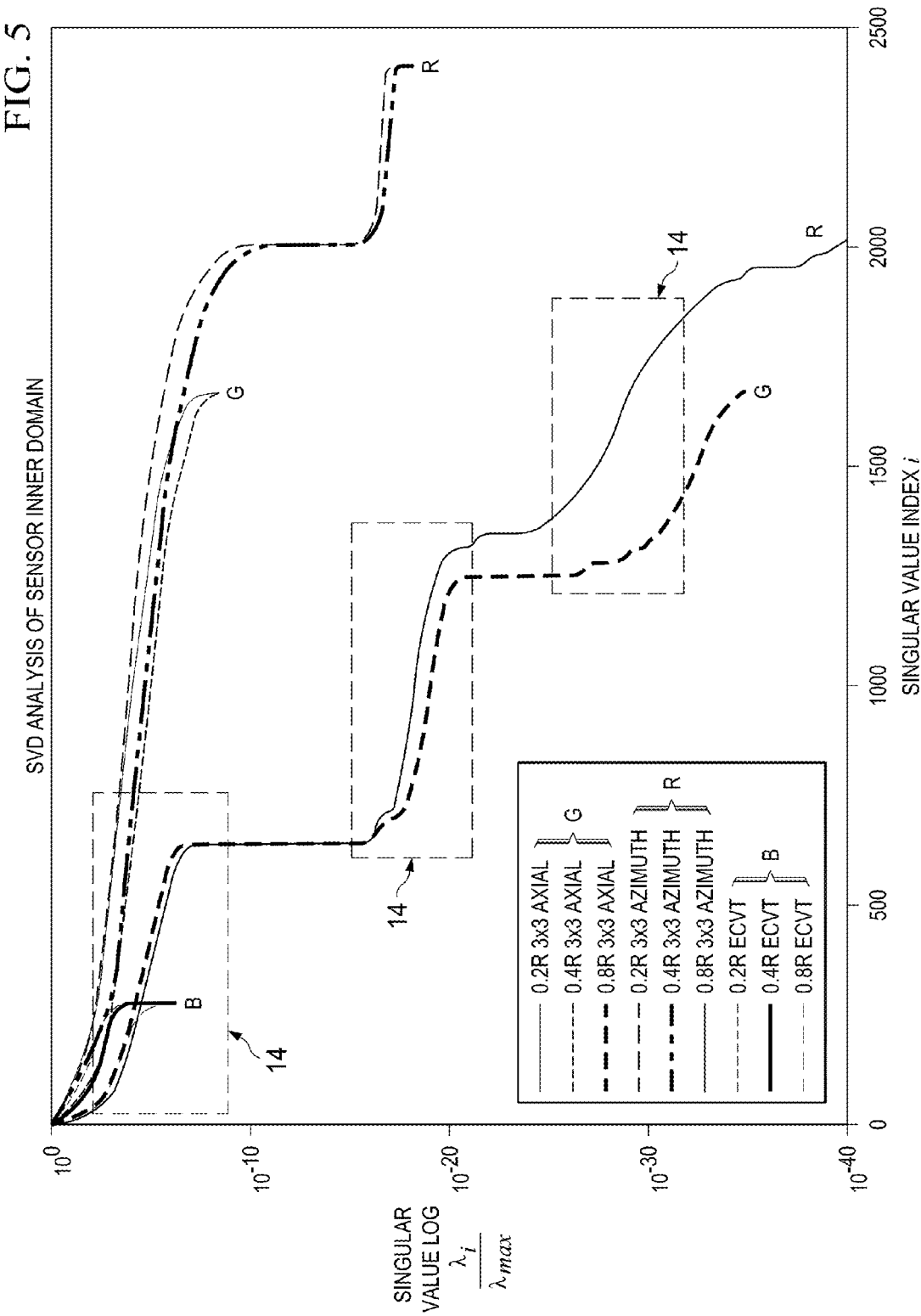

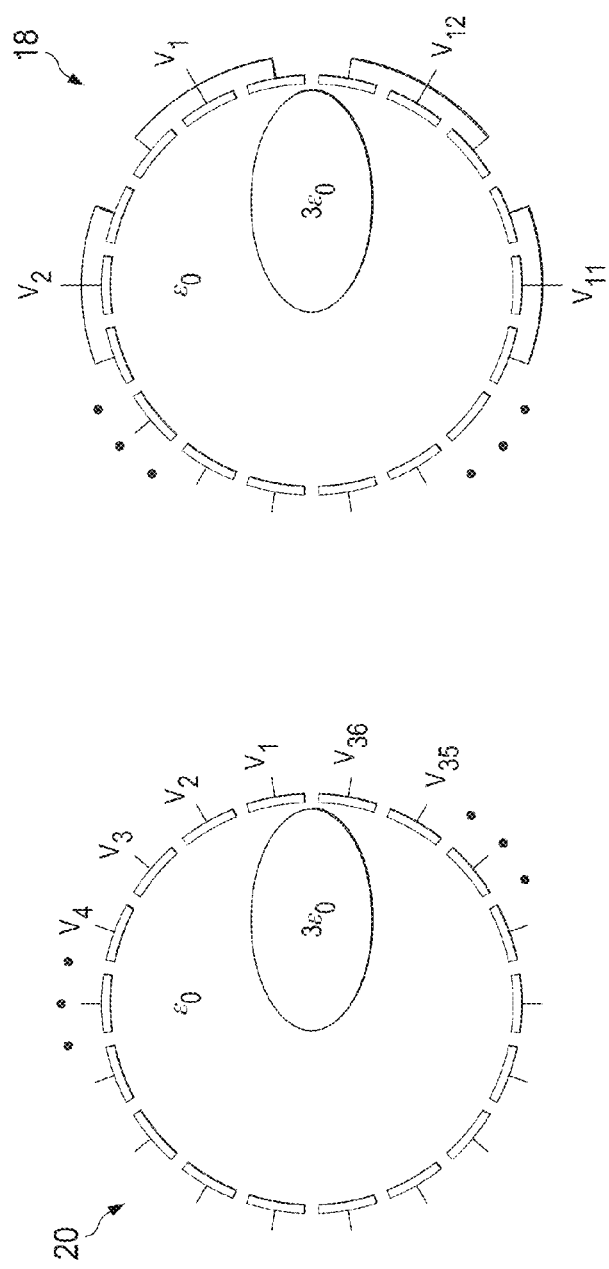
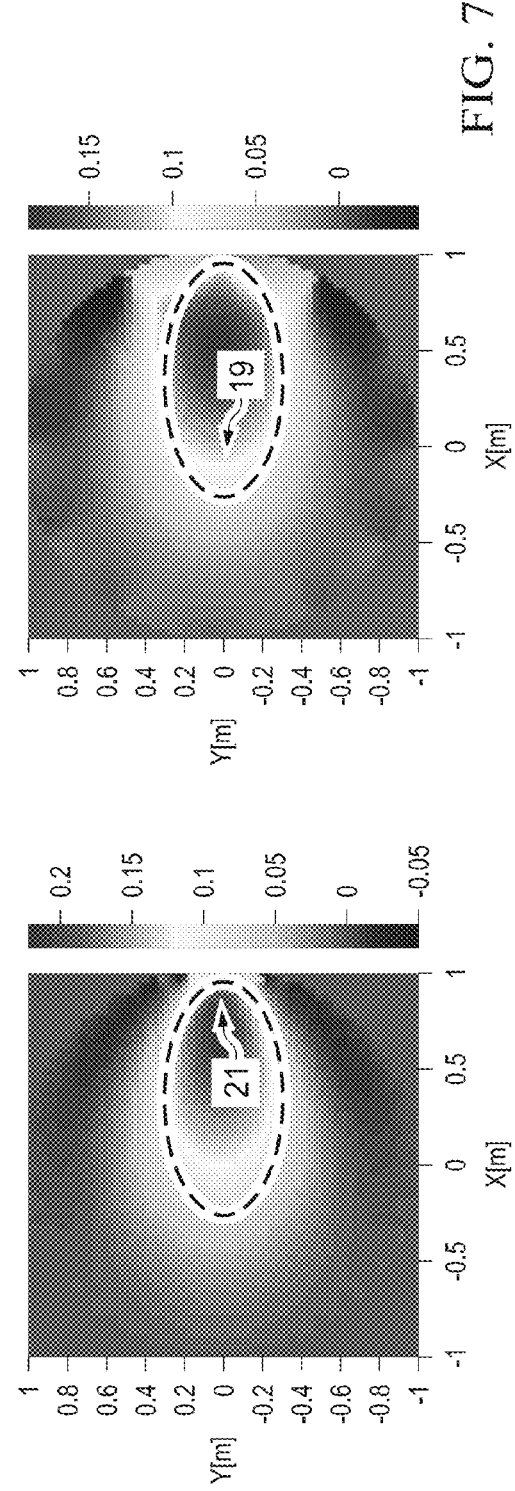
FIG. 7

SPACE ADAPTIVE RECONSTRUCTION TECHNIQUE FOR ADAPTIVE ELECTRICAL CAPACITANCE VOLUME TOMOGRAPHY

BACKGROUND AND SUMMARY OF THE INVENTIVE FIELD

Electrical Capacitance Volume Tomography (ECVT) is a non-invasive imaging modality. Its applications span an array of industries. Most notably, ECVT is applicable to multiphase flow applications commonly employed in many industrial processes. ECVT is often the technology of choice due to its advantages of high imaging speed, scalability to different process vessels, flexibility, and safety. In ECVT, sensor plates are distributed around the circumference of the column, object or vessel under interrogation. The number of sensor plates may be increased to acquire more capacitance data. However, increasing the number of sensor plates reduces the area of each sensor plate accordingly. A limit exists on the minimum area of a sensor plate for a given column diameter, thus limiting the maximum number of plates that can be used in an ECVT sensor. This limit is dictated by the minimum signal-to-noise ratio requirement of the data acquisition system. Since ECVT technology is based on recording changes in capacitance measurements induced by changes in dielectric distribution (i.e., phase distribution), and the capacitance level of a particular sensor plate combination is directly proportional to the area of the plates, minimum signal levels are needed to provide sufficiently accurate measurements. These considerations dictate the required minimum sensor plate dimensions. This limitation on the minimum size of the sensor plates, while increasing the number of available sensor plates in an ECVT sensor, is one of the main hurdles in achieving a high resolution imaging system.

To overcome this challenge, the concept of Adaptive Electrical Capacitance Volume Tomography (AECVT) was recently developed, whereby the number of independent capacitance measurements is increased through the use of reconfigurable synthetic sensor plates composed of many smaller sensor plates (constitutive segments). These synthetic sensor plates maintain the minimum area for a given signal-to-noise ratio (SNR) and acquisition speed requirements while allowing for many different combinations of (synthetic) sensor plates in forming a sensor plate pair.

Electrical Capacitance Tomography (ECT) is the reconstruction of material concentrations of dielectric physical properties in the imaging domain by inversion of capacitance data from a capacitance sensor. Electrical Capacitance Volume Tomography or ECVT is the direct 3D reconstruction of volume concentrations or physical properties in the imaging domain utilizing 3D features in the ECVT sensor design. ECVT technology is described in U.S. Pat. No. 8,614,707 to Warsito et al. which is hereby incorporated by reference.

Adaptive Electrical Capacitance Volume Tomography (AECVT) provides higher resolution volume imaging of capacitance sensors based on different levels of activation levels on sensor plate segments. AECVT is described in U.S. Patent Application Publication US2013/0085365 A1 to Marashdeh et al. which is hereby incorporated by reference.

In ECT, ECVT, or AECVT, the capacitance measurement between sensor plates is also related to the effective dielectric content between that plate pair. The SART method can be extended to all measurements of ECT, ECVT, or AECVT sensors, thus providing a high resolution visual representation of each phase through image reconstruction.

Synthetic sensor plate formation is possible through advancements in the data acquisition technology that have enabled rapid separation in activation sources and the combination of the aggregated response from each segment of a given synthetic sensor plate. The total area of the segments combined can be made equivalent (or close) to that of a conventional ECVT sensor plate. Adaptive sensor plates can be used to increase the number of capacitance measurements and hence yield overall higher resolution imaging. Furthermore, AECVT plates can be used to adaptively modify the sensitivity of the output current to specific regions of interest in the imaging domain (where enhanced selective resolution may be desired) through the use of appropriate voltage patterns applied to the set of excitation sensor plates. To construct such voltage patterns, each segment is activated by different voltage levels thus forming a new sensitivity map. The use of different voltage patterns among individual segments that comprise a sensor plate also allows for a gradual taper of voltage levels between any two adjacent segments. This gradual tapering permits the use of higher peak voltages, and consequently increased SNR, without risk of dielectric breakdown (electrostatic discharges) occurring between the said segments.

AECVT is a novel technology that provides a significant increase in the number of possible independent capacitance measurements. However, increasing the number of independent measurements using AECVT technology only partially solves the resolution problems in capacitance-based tomography. Resolution is affected and determined by two other factors, in addition to AECVT sensor design: 1) suitable image reconstruction algorithms that can exploit the increase in information available from AECVT sensors, and 2) customized electronic design of high-speed measurement circuits utilized for AECVT sensors. The present invention specifically relates to the first factor above and comprises a new Spatial-Adaptive Reconstruction Technique (SART), which introduces a new image reconstruction technique that can take full advantage of the measurement capabilities provided by the AECVT sensor hardware design to achieve higher resolution imaging.

Extensive research has been done in the field of image reconstruction including non-iterative and iterative techniques. The most basic non-iterative image reconstruction technique is called Linear Back Projection (LBP) and is based on the assumption that a sensor can be modeled as a linear system where the overall capacitance change can be attributed to the linear superposition of local perturbations in the permittivity distribution within the imaging domain. Although LBP is able to provide very fast reconstruction, it gives very inaccurate reconstruction results when the spatial volume fraction, comprising the permittivity perturbation inside the imaging domain, is large and/or when the value of the relative permittivity of the said permittivity distribution is large. In addition to the LBP technique, Singular Value Decomposition (SVD) and Tikhonov methods have been used to regularize the final reconstructed image and to reduce the degree of ill-posedness of the problem. Moreover, to overcome the non-linearity of the problem, iterative reconstruction techniques also have been adopted. For example, Levenburq-Marquardt optimization techniques and Landweber techniques, based on the steepest gradient descent method, are used to minimize the squared error between measured and calculated capacitance data iteratively. Although iterative reconstruction techniques provide a better resolution compared to non-iterative reconstruction techniques, the former have convergence problems and require more computation time, which can be a drawback for some applications requiring real-time imaging. Historically, the resolution of either iterative or non-iterative techniques is limited by the soft-field nature of capacitance tomography, and by the ill-posedness and ill-conditioning of the inverse problem. The soft-field nature is related to the resolution being limited at the center of the imaging domain due to the Laplacian nature of the quasi-static field that interrogates the imaging domain (which has a self-averaging property of minimizing the average value taken over the surrounding points). This precludes the use of phase information and constructive/destructive interference to achieve focusing in certain regions of the domain (as can be done, for example, in microwave tomography). The present invention relates to new reconstruction algorithms poised to exploit the additional degree of freedom provided by the AECVT measurement acquisition hardware.

The new reconstruction methodology of the present invention, SART, is designed to utilize the flexibility of the AECVT technique in such a way that the imaging domain is divided into several regions where each region's permittivity distribution is reconstructed independently, based on "a priori" information about other region's calculated permittivity distributions. The algorithm iteratively reconstructs the spatial permittivity distribution of each separate region in the imaging domain until convergence is achieved. This process may also involve staggered iterative methods where each region is reconstructed iteratively and the independent regions are then combined into one image through another iterative optimization process. The basic principle behind this new reconstruction algorithm is that the fundamental resolution provided by the segment plates decreases monotonically from the periphery of the imaging domain close to the segment plates toward the center of the imaging domain far from the segment plates, due to the Laplace nature of interrogating the quasi-static electric field. Therefore, in electrical capacitance tomography applications, the field lines that penetrate into the middle of the imaging domain are always weaker and more spread-out compared to those closer to the sensor plates. The spatial sensitivity of any given capacitance sensor plates (to permittivity variations) is much greater at points in close vicinity to it when compared to points farther away from it. This causes the image resolution to progressively degrade at regions further away from the sensor plates.

By utilizing the SART method of the present invention and the reconfigurability of AECVT sensors, the sensitivity and hence resolution at the center of the imaging domain can be increased by taking advantage of information provided by an "a priori" reconstruction of the peripheral region. By utilizing near and adjacent plates, the overall resolution can be improved iteratively. As noted, iterative methods into themselves are not new in the field of electrical tomography systems. For example, the Distorted Born Iterative Method (DBIM) was used in impedance tomography reconstruction. However, those methods neither iterate over spatial regions adaptively nor exploit the flexibility of different excitation patterns enabled by AECVT.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein:

FIG. 5 illustrates SVD analysis of simulated data from sensors with plate formations similar to FIG. 3A and FIG. 4A. The SVD plot shows that capacitance values can be categorized based on their SVD values.

FIG. 7 a reconstruction result of an object that extends into the center of the imaging domain.

DETAILED DESCRIPTION OF EXEMPLARY EMBODIMENT(S)

Figure 1A:
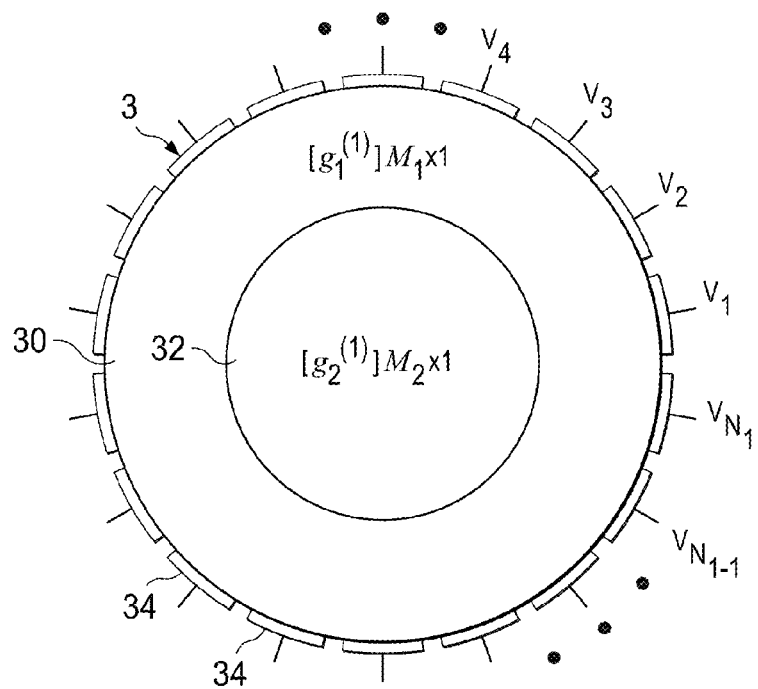
FIGS. 1A and 1B illustrate two views of one embodiment of a cross-section of sensor of the present invention illustrating the spatial-adaptive regions for two plate geometries.
Figure 1B:
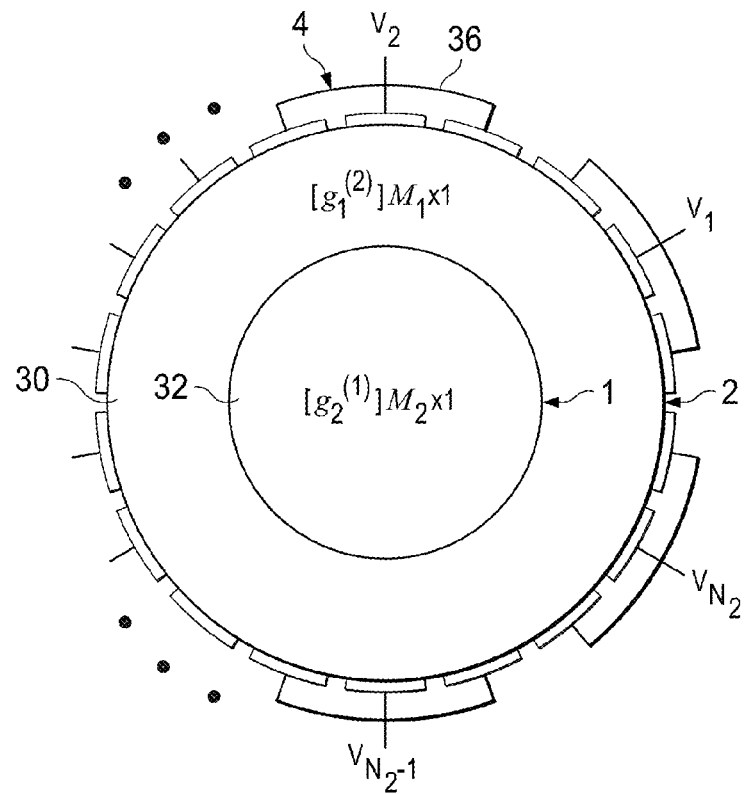

FIGS. 1A and 1B illustrate two views of one embodiment of a cross-section of sensor of the present invention illustrating the spatial-adaptive regions (1, 2) for two plate geometries (3, 4). The plate geometry of small segments (3) is used to reconstruct spatial region 2. The plate geometry of larger plates (4) is used to reconstruct spatial region 1. SART reconstruction relies on different plate activations for reconstructing different spatial regions.

FIGS. 1A and 1B illustrate one embodiment of the SART method where two regions of reconstruction are identified, a peripheral region $R_1$ denoted at (30), and a center region $R_2$ denoted at (32). For reconstruction of the peripheral region $R_1$, small individual sensor plate segments can be utilized, as indicated in the plot the at left where each sensor plate segment (34) is assigned an independent source voltage V. Alternatively, to reconstruct the center region $R_2$, larger synthetic sensor plates can be utilized comprised by many small segments combined together (36), as illustrated in the plot at the right by the sets of three joined segments, with unique applied voltage sources. The peripheral and center regions can be reconstructed in different steps and utilizing different sets of capacitance data as identified using SVD analysis. Reconstructed regions in previous steps can be used as a priori information for reconstructing different regions in a subsequent step. Without loss of generality, the imaging domain can be divided in more than two regions and into regions of different shapes (that are not necessarily circular).

Figure 2A:
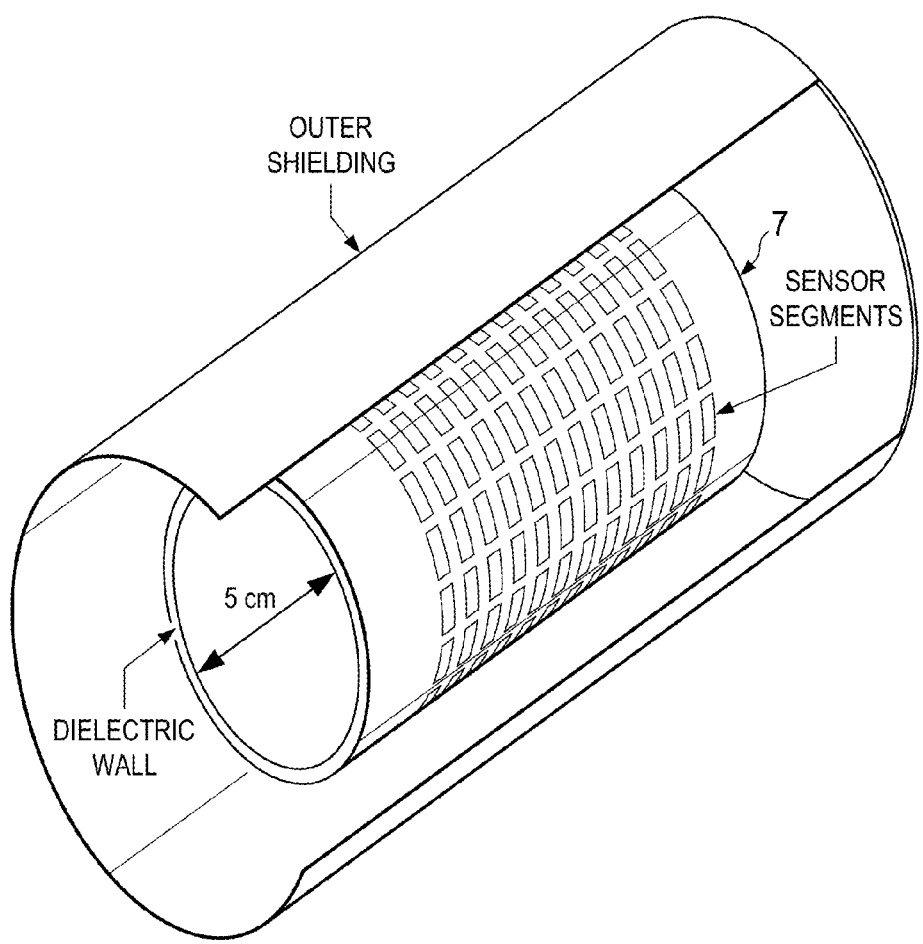
FIG. 2A illustrates the embodiment of the adaptive sensor where many small segment plates are combined together to form larger synthetic plates.
Figure 2B:
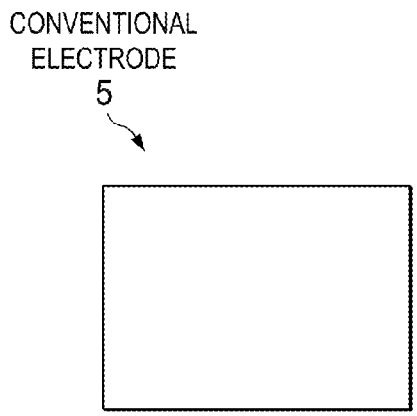
FIG. 2B shows one embodiment of an electrode of the present invention.
Figure 2C:
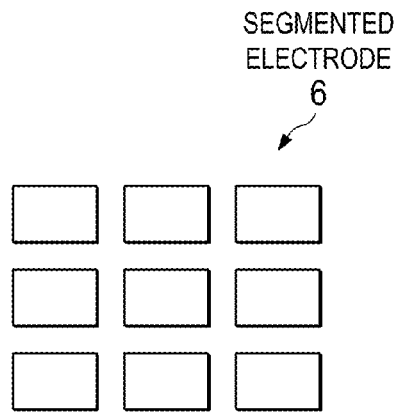
FIG. 2C shows one embodiment of a segmented electrode of the present invention.

FIG. 2A illustrates one embodiment of an AECVT sensor of the present invention. FIG. 2B shows one embodiment of an electrode (5) or conventional plate of an ECVT sensor of the present invention. FIG. 2C shows one embodiment of a segmented electrode (6) of the AECVT sensor of the present invention.

An adaptive sensor (7) is formed of many small plate segments. By applying voltages to various combinations of plate segments in the AECVT sensor, different plate geometries can be used for reconstructing different regions using the SART algorithm. In the preferred embodiment, there is one voltage source connected to all segments. However, the voltage is attenuated or amplified before each segment such that segments will have different voltage levels. For example, for each segment there is an amplifier or attenuator that determines how much voltage is being switched on and applied to each segment. It is the combination of both (switches and voltage level control) that enables AECVT. The SART technique can also be used with conventional ECVT, however, the resolution would be much less in this case compared to AECVT.

The many small segment plates of the adaptive sensor may be combined together to form larger synthetic plates. This arrangement enables increased flexibility by forming plates of different sizes and shapes, and by using different activation levels on the individual segments that form a given synthetic plate.

Figure 3A:
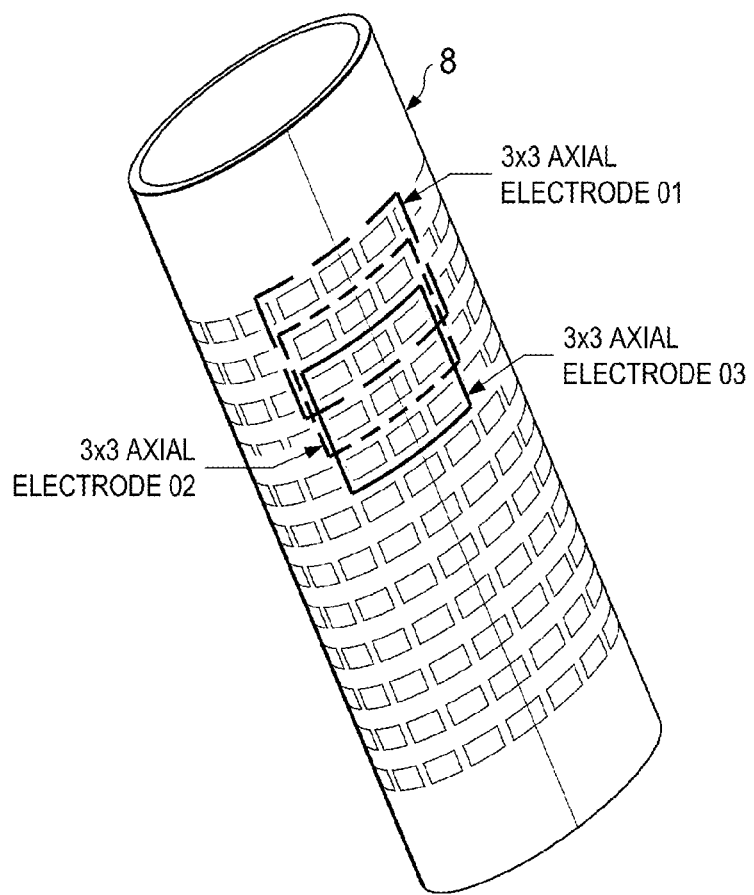
FIG. 3A illustrates one embodiment of a sensor of the present invention showing various plate formations in the axial direction of the sensor by combining small segments in different formations.
Figure 3B:
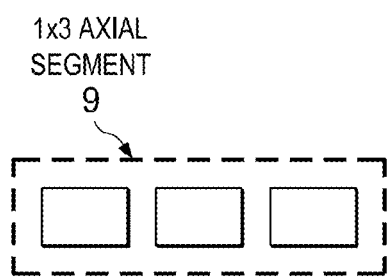
FIGS. 3B and 3C illustrate various groupings of capacitive segments of the sensor.
Figure 3C:
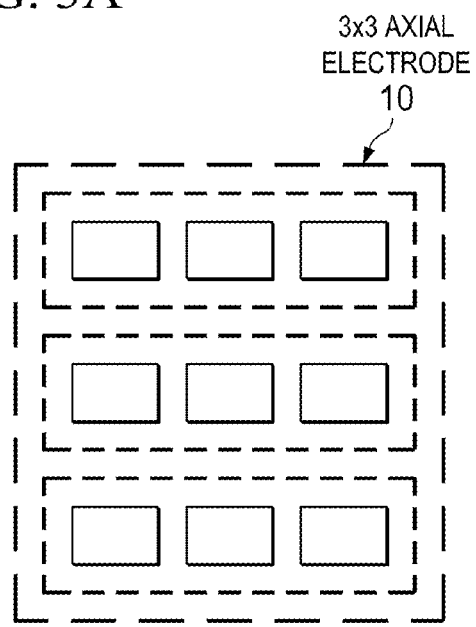

FIG. 3A illustrates one embodiment of a sensor of the present invention showing various plate formations in the axial direction of the sensor by combining small segments in different formations (9, 10). FIGS. 3B and 3C illustrate various groupings of capacitive segments of the sensor. As discussed, different shapes or sizes of plate segments can be created by applying voltages to any combination of segments. An illustration of electronically shifting plate formations in the axial direction is also illustrated (8). FIG. 3C illustrates how a synthetic plate composed of 3×3 segments in a AECVT sensor can be reconfigured electronically into Electrodes 01, 02, and 03 to simulate plate movement, in smaller increments, along the vertical direction and thereby provide more capacitance data to enable higher resolution imaging. FIGS. 3A, 3B and 3C also show that plates of different sizes and shapes can be synthesized from the small segments, as exemplified by the 1×3 segment combination denoted as (9), and the 3×3 segment combination denoted as (10).

Figure 4A:
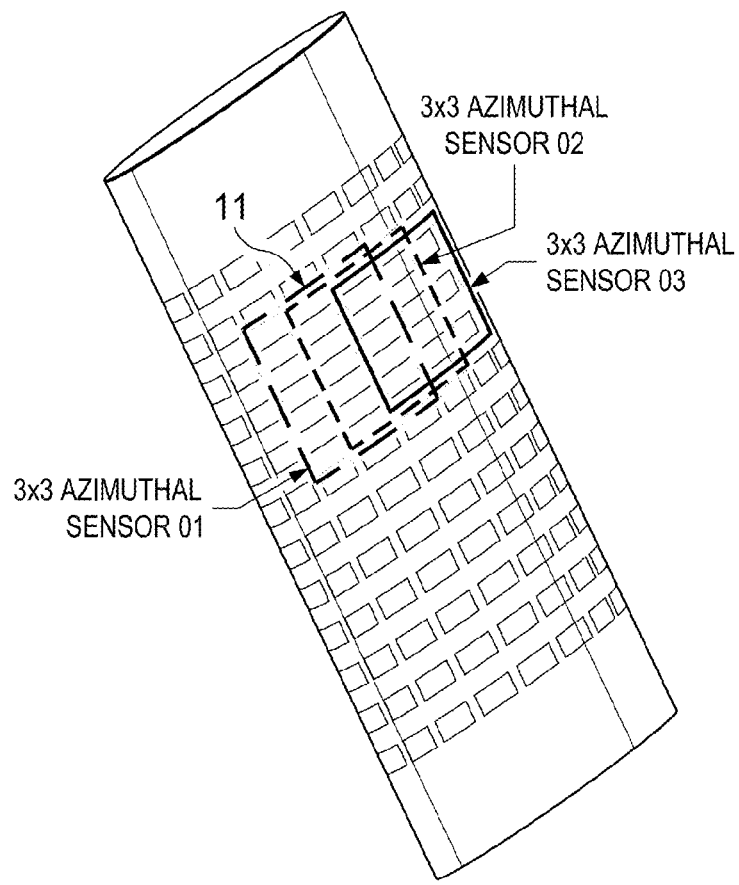
FIG. 4A illustrates one embodiment of a sensor of the present invention illustrating various plate formations in the azimuthal direction through combining small plate segments in different formations.
Figure 4B:
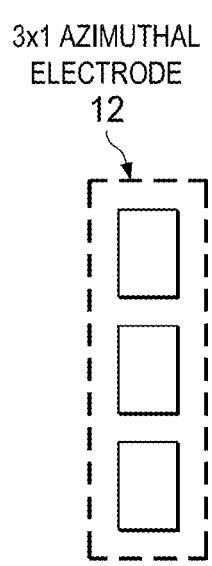
FIGS. 4B and 4C illustrate various groupings of capacitive segments of the sensor.
Figure 4C:
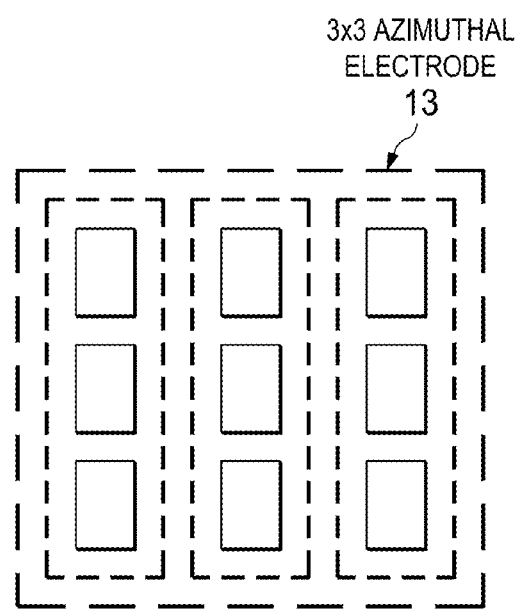

FIG. 4A illustrates one embodiment of a sensor of the present invention illustrating various plate formations in the azimuthal direction through combining small segments in different formations (12, 13). FIGS. 4B and 4C illustrate various groupings of capacitive segments of the sensor. An illustration of electronically shifting plate formations in azimuthal direction is also provided (11). FIGS. 4A, 4B and 4C illustrate how a synthetic plate composed of 3×3 segments in a AECVT sensor can be reconfigured electronically into Electrodes 01, 02, and 03 to simulate plate movement, in smaller increments, along the angular (or azimuthal) direction and thereby provide more capacitance data to enable higher resolution imaging. FIGS. 4A, 4B and 4C also show that plates of different sizes and shapes can be synthetized from the small segments, as exemplified by the 3×1 segment combination denoted as (12), and the 3×3 segment combination denoted as (13).

FIG. 5 illustrates a typical graph of different SVD levels resulting from various plate combinations (14). Each level of SVD corresponding to plate activations is related to a specific region in SART reconstruction. Reconstruction is decomposed into different regions based on SVD analysis.

Figure 6:
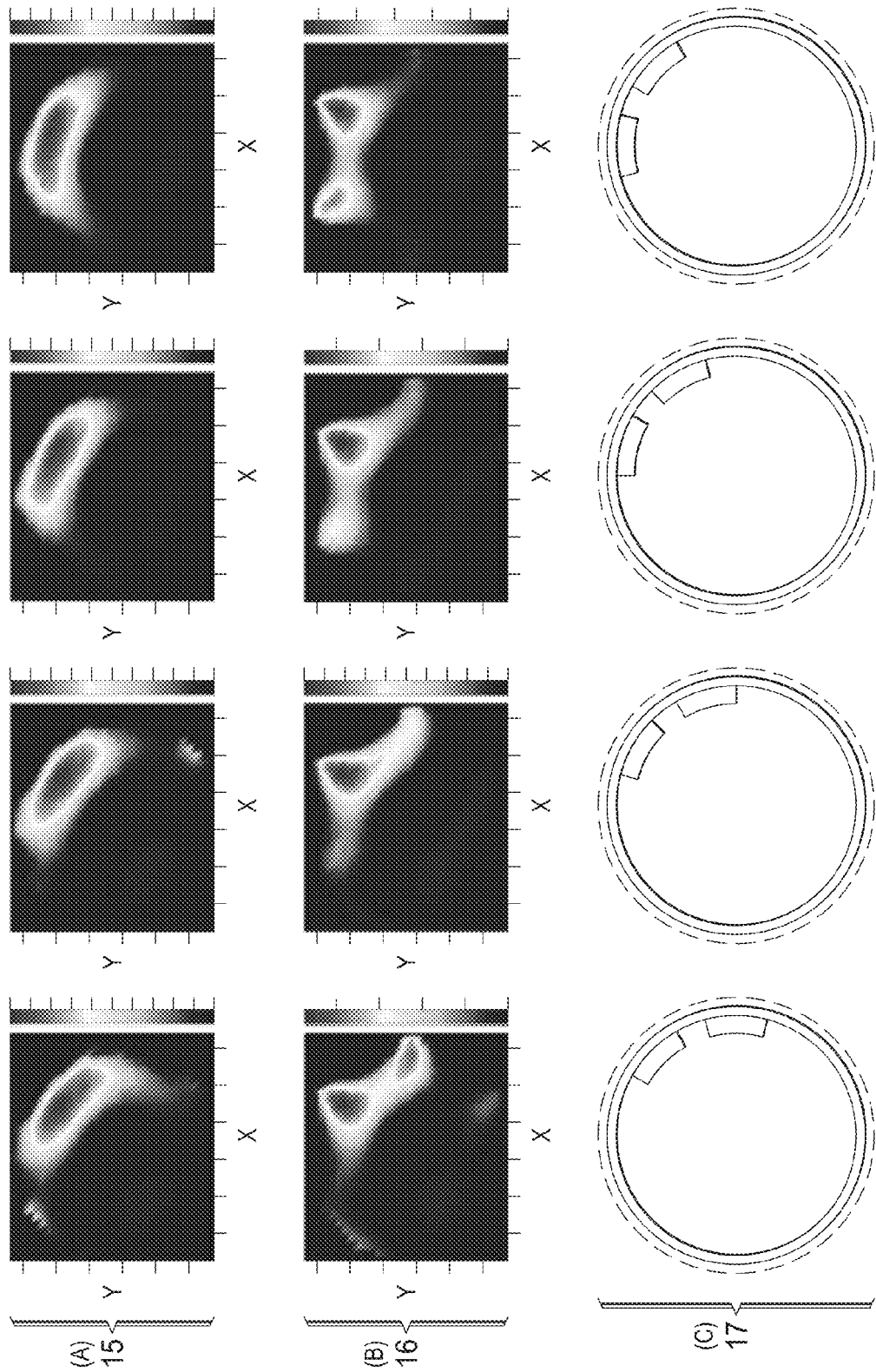
FIG. 6 illustrates one embodiment of small plates used to reconstruct objects near to the sensor plates, with higher resolution.

FIG. 6 illustrates a reconstruction result of sensed objects near the sensors in region (2) of FIGS. 1A and 1B. Higher resolution is obtained (15) by using small segment activations in (17). Original shapes simulated here are depicted in (17). This increase in resolution is compared to conventional ECVT sensor resolution (16). Each level of SVD corresponding to plate activations is related to a specific region in SART reconstruction. Reconstruction is decomposed into different regions based on SVD analysis.

FIG. 7 illustrates a reconstruction result of an object that extends into the center of the imaging domain. Two plate activations are used, small segment (20) and large plates (18). The simulated object is in both regions (1) and (2) of FIGS. 1A and 1B. Higher resolution is obtained in region (2) when small segment activation is used, as depicted in (21). Higher resolution is obtained in region (1) toward the center of the sensor when large plate activation is used, as depicted in (19).

Figure 8:
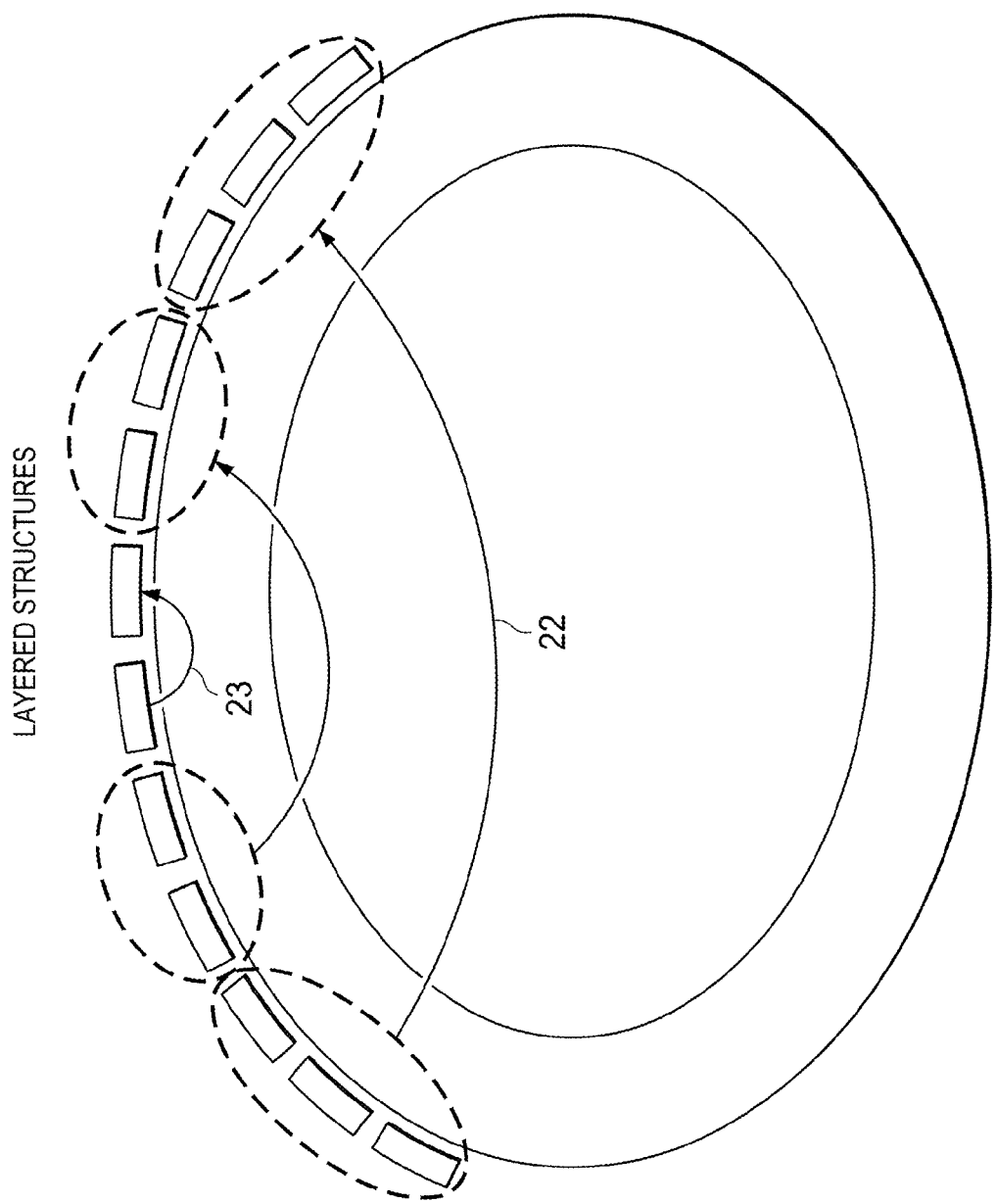
FIG. 8 illustrates one embodiment of SART activation with reconfigurable AECVT sensor plate segments for a layered structure.

FIG. 8 illustrates a layered structure where some activations are attributed to an inner layer (22) and some activations are attributed to outer layer (23). SART can be used to reconstruct those distinct regions based on SVD analysis of plate combinations for capacitance measurements. (SART can be used to identify the boundary between those distinct regions based on SVD analysis and plate activations as described above).

Examples illustrating the validity and suitability of the new SART technique for image reconstruction from AECVT data are demonstrated in FIGS. 6 and 7. In FIG. 6, the imaging resolution of the reconstructed shapes near the sensors is much higher when smaller segment plates enabled by AECVT sensors are utilized, compared to conventional ECVT plates. However, in FIG. 7, the resolution toward the center of the imaging domain is actually better when larger plates are used, especially when those larger plates are separated away from each other. Those observations can be exploited by using AECVT sensors with reconfigurable sensor plates of various sizes and separations, together with the new SART reconstruction technique for conducting discriminate reconstruction based on spatial sensitivity of each plate formation used to acquire a measurement from an AECVT sensor.

In the process of reconstructing each independent spatial region alone, singular value decomposition (SVD) is used to analyze and classify capacitance measurements according to their spatial significance. SVD decomposes the capacitance measured data into a set of eigenvectors and corresponding eigenvalues $\lambda_i$. These eigenvalues can be arranged in the order of importance, e.g. according to their relative magnitudes $|\lambda_1| \geq |\lambda_2| \geq |\lambda_3| \ldots |\lambda_N|$. Capacitance measurements that correspond to lower singular values are regarded as providing less information compared to capacitance measurements that have higher singular values. In other words, capacitance measurements that have lower singular values may have useful information, but their information is masked by other capacitance measurements that have higher singular values, when analyzed together. In the SART technique, capacitance values are divided into independent reconstruction problems for specific spatial regions. Thus, a collection of capacitance measurements would yield much more information when combined with other measurements of the same SVD rank.

An alternative embodiment of the present invention may also be used where capacitance plates are selectively activated where higher resolution is required. (This activation is dictated by a co-design approach in which the SART algorithm will identify regions in the imaging domain where higher resolution is required, and thus determine required activations for providing such activations.) This activation is dictated by SVD rank of such measurements and their relation to spatial location where the higher resolution is required. An illustration is provided in FIG. 5 where SVD values undergo steep changes at different regions. Capacitance values in each group of similar SVD rank correspond to the same regions in the imaging domain. Separating those regions based on SVD analysis into separate reconstruction zones drastically enhances the contribution of lower SVD values by increasing the resolution in regions in the imaging domain that are farther away from the sensor plates.

In SART reconstruction, different regions of the domain can be reconstructed asynchronously. Regions that are reconstructed first are considered as a priori information for successive reconstruction of the following regions in the imaging domain. For example, consider regions $R_1$ and $R_2$ in FIGS. 1A and 1B. The first reconstruction can correspond to region $R_1$ and based on selected capacitance measurements from SVD analysis. This can be expressed as:

$$G_1 = f(C_1) \quad (1)$$

where $G_1$ is the reconstructed image for region $R_1$, f is a generic reconstruction algorithm function that can be either iterative of non-iterative, and $C_1$ is the optimal selected subset of measured capacitance values that correspond to $R_1$, as established by the SVD analysis. Next, for region R2:

$$G_2 = f(G_1, C_2) \quad (2)$$

where $G_2$ is the image reconstruction result of region 2, f is again a generic reconstruction function that can be either iterative or non-iterative, $G_1$ is the reconstructed result of region 1, and $C_2$ is the optimal reconfigured capacitance data set corresponding to region $R_2$, as established by the SVD analysis. The inclusion of $G_1$ in the reconstruction function of $G_2$ refers to using result of $G_1$ as a priori information for generating sensitivity matrix that will be used in reconstruction of $G_2$. This means that the information provided by $G_1$ is included in any forward solution required in iterative reconstruction of $G_2$.

For iterative reconstruction, one embodiment can include $G_1$ reconstructed iteratively until convergence is reached. Using this converged result for $G_1$, $G_2$ is then reconstructed iteratively until convergence is reached. An optimization step can be used to merge results from $G_1$ and $G_2$ into one final image.

Another embodiment for iterative reconstruction can include staggered iterations where, in the first iteration: 1) $G_1$ is solved for, 2) $G_1$ is used together with $C_2$ for reconstructing $G_2$, 3) the reconstruction result for $G_2$ is then fed back to solve for $G_1$ using $C_1$ in a new iteration. Mathematically, the formulation in this case would read:

$$G_1^r = f(G_2^{r-1}, C_1) \quad (3)$$

$$G_2^r = f(G_1^{r-1}, C_2) \quad (4)$$

where r is iteration number. Without loss of generality, SART method can be similarly extended to more than two reconstruction regions.

The present invention also provides a method for identifying boundaries between different layers in a layered structure. For example, the human body is formed from different layers (skin, fat, bone etc) that are layered from the outside inward. As different layers have different electrical properties (dielectric constant and conductivity), the SART method can be used to target each layer independently by means of reconfigured AECVT measurements. The SART method can also be used here to identify boundaries between layers for better imaging. Those boundaries can also be integrated in a global volume image where all layers are viewed simultaneously.

Figure 9:
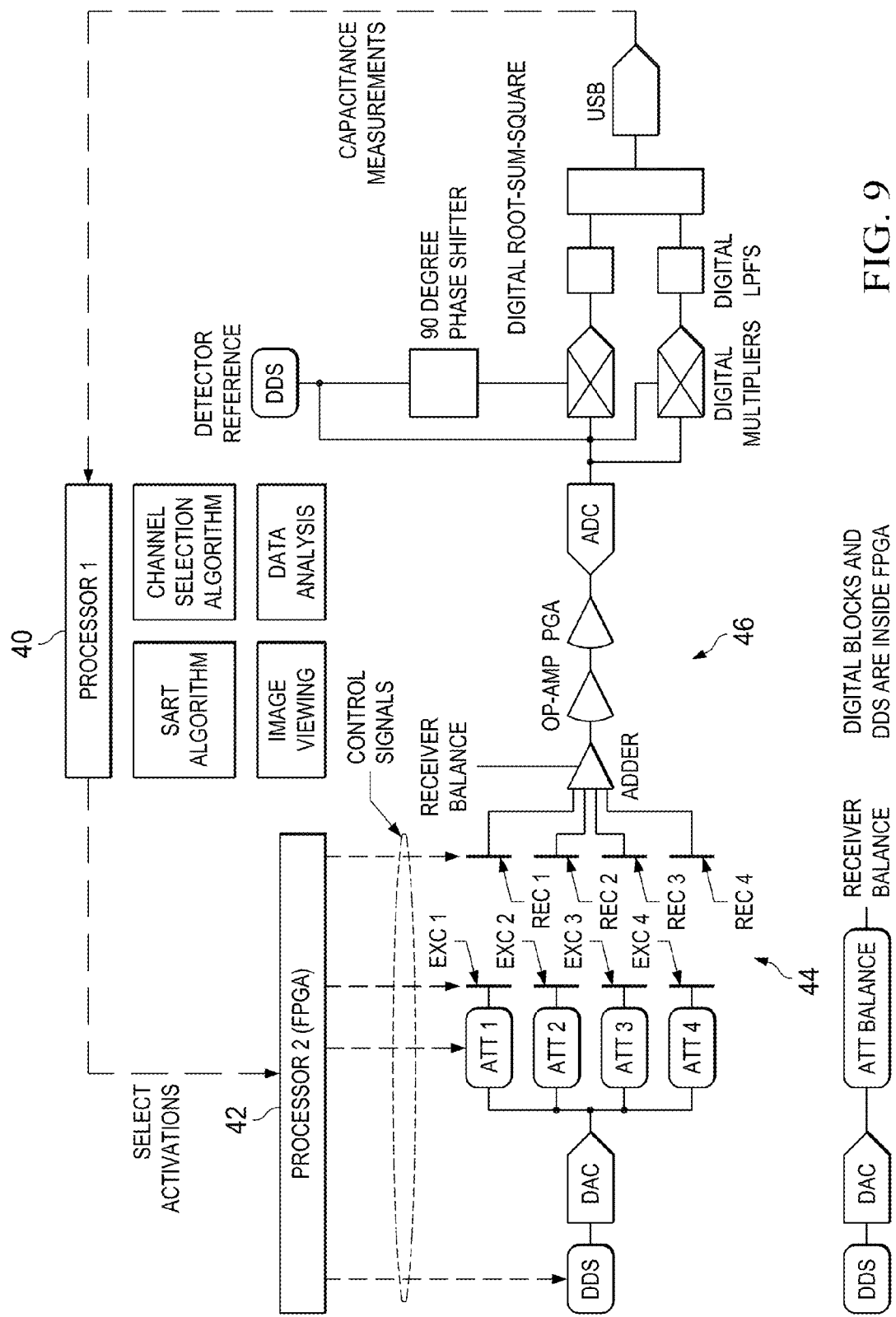
FIG. 9 illustrates one embodiment of the block diagram of the system of the present invention.

FIG. 9 illustrates one embodiment of the block diagram of the system of the present invention. The system is comprised of a first processing system (40), a second processing system (42), a sensor having a plurality of electrodes (shown generally at 44), a data acquisition circuit/measurement circuit (shown generally at 46). The first processing system can be a personal computer (PC), tablet, or smart phone. The first processing system is connected to the output of the system to receive the data input relating to the capacitance measurements. The first processing system is preferably programmed with a channel selection algorithm and the SART algorithm of the present invention. The second processing system may be implemented via a field programmable gate array (FPGA) and preferably receives the control signals from the first processing system to control activation of the electrodes or capacitance segments of the sensor.

The plurality of electrodes form a plurality of capacitance segments where the electrodes are individually addressable with voltages. The data acquisition electronics, in communication with the output of the three-dimensional capacitance sensor device, receives input data from the three-dimensional capacitance sensor device. The system also preferably comprises a tunable band pass filter in electrical communication with the output of the three-dimensional capacitance sensor device wherein the first processing system is programmed with instructions for executing on the processing system to reconstruct the permittivity distribution and an image of the imaging region based on the measured capacitance.

The system also preferably comprises a phase shifter in electrical communication with the input of the three-dimensional capacitance sensor device for synchronizing with the active electricity; and attenuators (48) in electrical communication with the input of the three-dimensional capacitance sensor device for detecting an amplitude of active electricity. The attenuators may be used to control the level of activation or voltage applied and to control sensor sensitivity as discussed.

The three-dimensional capacitance sensor device comprising a plurality of electrodes for placement around the vessel or the object is adapted to provide electric field distribution and sensor sensitivity in three geometric dimensions. As illustrated in FIGS. 2A and 3A, the three-dimensional capacitance sensor device is preferably comprised of multiple planes of electrodes to provide sensor sensitivity in the axial and radial directions. The data acquisition electronics in communication with the three-dimensional capacitance sensor device receives input data from the three-dimensional capacitance sensor device; and the first processing system, in communication with the data acquisition electronics, reconstructs a three-dimensional volume-image from the input data collected by the data acquisition electronics. The first processing system is programmed to calculate capacitance data from the input data received by the data acquisition electronics. The image reconstruction algorithm is adapted to provide real-time imaging of multiphase flow within the vessel.

In the preferred embodiment, the SART algorithm discussed in the present application, the image reconstruction process, the data analysis, and algorithm for selecting required activations (of electrodes for ECVT sensors or capacitance plate segments for AECVT sensors) are all in the first processing system. The second processing system receives the signals for activating electrodes or capacitance plate segments and acts to implement them toward capacitance measurements. The SART processor connects to the FPGA, which controls each of the switches and attenuators (or amplifiers) to control which segments are activated and by how much. The FPGA implements activation patterns based on feedback from the SART processor.

There are multiple ways the first processing system (with the SART algorithm) and the FPGA can interact. For example, 1—The FPGA can activate many measurements by implementing pre-programmed patterns, and the first processing system using the SART algorithm will only use those that are suitable for image reconstruction in the proposed SART form; or 2—By interacting with the data acquisition system through the FPGA and requesting specific measurements of segments and activation as shown in FIG. 9.

Figure 10:
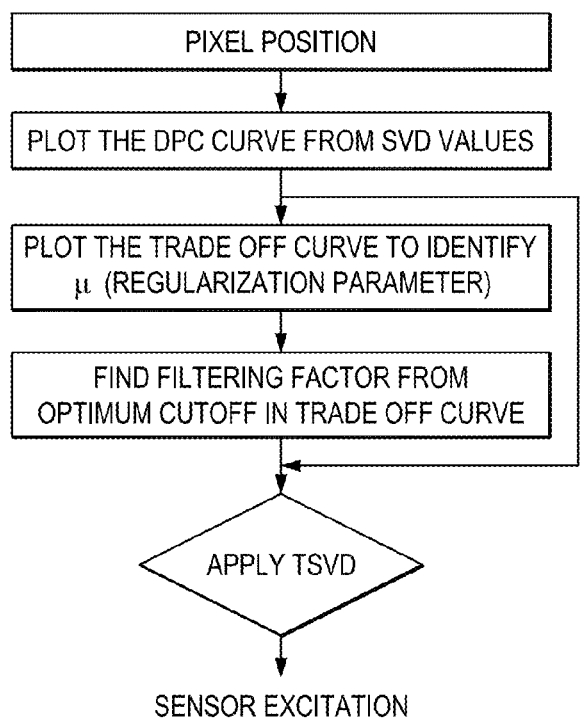
FIG. 10 illustrates a process according to the present invention for relating pixel position to the required activation for providing enhanced resolution.

FIG. 10 illustrates a process according to the present invention for relating pixel position to the required activation for providing enhanced resolution. The steps involve:

1—Obtain pixel position;
2—Plot the Discrete Picard Condition (DPC) from SVD values (DPC for determining stability condition of SVD);
3—Plot the trade off curve to identify the regularization parameter;
4—Find the filtering factor from optimum cut-off in the trade off curve;
5—Apply the truncated SVD to determine required activation.

While certain embodiments of the present invention are described in detail above, the scope of the invention is not to be considered limited by such disclosure, and modifications are possible without departing from the spirit of the invention as evidenced by the following claims.

What is claimed is:

1. A system for tomographic imaging in a pipe, tube or other object comprising:
    a sensor, comprising at least four electrodes, positioned in a predetermined arrangement relative to each other around the pipe, tube, or object; each of the electrodes comprising a plurality of capacitance plate segments, each of the capacitance plate segments of each of the electrodes defining a capacitor when paired with a corresponding capacitance plate segment of one of the other electrodes;
    a voltage source, arranged to impart a voltage to selected capacitance plate segments, a sensitivity of the sensor being controlled by at least one of: the amount and the distribution of the imparted voltage applied to the selected capacitance plate segments;
    a measuring circuit, connected to each of the at least four electrodes to detect a capacitance of any of the capacitors between any selected pair of the electrodes though currents induced in the measuring circuit; and
    a first processing system, in communication with the measuring circuit, the first processing system programmed with instructions for executing on the first processing system to: 1) convert capacitance data collected therefrom into an image; 2) analyze information provided by an image reconstruction of a peripheral region of an imaging domain of the sensor; and 3) provide control signals to the sensor to increase the resolution at a center region of the imaging domain of the sensor based on the prior image reconstruction of the peripheral region; 4) obtain image reconstruction information for the center region of the imaging domain; and 5) combine the image reconstruction information for the peripheral region and the center region to obtain a combined image of the imaging domain.

2. A system for tomographic imaging according to claim 1, wherein the sensitivity of the sensor can be controlled by changing the frequency of the voltage distribution applied to at least one electrode.

3. A system for tomographic imaging according to claim 1, wherein the system is adapted to activate one electrode at a time as a source electrode, one electrode as the detecting electrode, and wherein the detecting electrode is connected to the measuring circuit.

4. A system for tomographic imaging according to claim 1, wherein the system is configured to obtain the capacitance between all the electrodes and to reconstruct an image of the region between the electrodes based on the capacitances obtained.

5. A system for tomographic imaging according to claim 1, wherein each capacitance plate segment of each electrode is individually addressable by a voltage that is connected to each of the capacitance plate segments through a switch.

6. A system for tomographic imaging according to claim 1, wherein the electric field between two electrodes can be focused based on the voltage levels used to address the capacitance plate segments.

7. A system for tomographic imaging according to claim 1, further comprising a plurality of switches and amplifiers; wherein each capacitance plate segment is electrically connected to a switch and an amplifier and wherein the system is configured to turn each of the plurality of switches on to apply a voltage to the capacitance plate segment connected to it; and wherein each of the plurality of amplifiers control the amount of voltage applied to each capacitance plate segment.

8. A system for tomographic imaging according to claim 1, wherein the first processing system programmed with instructions for executing on the first processing system to selectively use capacitance measurements based on singular value decomposition analysis for reconstructing images that are spatially divided into distinct regions.

9. A system for tomographic imaging according to claim 1, wherein the first processing system programmed with instructions for executing on the first processing system to control activation of capacitance plate segments by using an evolution of a reconstructed image.

10. A system for tomographic imaging according to claim 1, wherein the first processing system programmed with instructions for executing on the first processing system to control activation of the capacitance plate segments to enhance resolution at specific regions in an imaging domain of the sensor based on feedback data received from the measuring circuit.

11. A system for tomographic imaging according to claim 1, wherein the first processing system programmed with instructions for executing on the first processing system to use singular value decomposition analysis to identify different categories of capacitance data and relate them to distinct regions in an imaging domain of the sensor.

12. A system for tomographic imaging in a pipe, tube or other object comprising:
- a sensor, comprising at least four electrodes, positioned in a predetermined arrangement relative to each other around the pipe, tube, or object, each of the electrodes defining a capacitor when paired with another electrode;
- a voltage source, arranged to impart a voltage to selected electrodes, a sensitivity of the sensor being controlled by at least one of: the amount and the distribution of the imparted voltage applied to the selected electrodes;
- a measuring circuit, connected to each of the at least four electrodes to detect a capacitance of any of the capacitors between any selected pair of the electrodes through currents induced in the measuring circuit; and
- a first processing system, in communication with the measuring circuit, the first processing system programmed with instructions for executing on the first processing system to: 1) convert capacitance data collected from the measuring circuit into an image; 2) analyze information provided by an image reconstruction of a first spatial region of an imaging domain of the sensor; 3) provide control signals to the sensor to increase the resolution at a second spatial region of the imaging domain of the sensor based on the prior image reconstruction of the first spatial region; 4) obtain image reconstruction information for the second spatial region of the imaging domain; and 5) combine the image reconstruction information for the first spatial region and the second spatial region to obtain a combined image of the imaging domain.

13. A system for tomographic imaging according to claim 12, wherein the first processing system is programmed with instructions for executing on the first processing system to selectively use capacitance measurements based on singular value decomposition analysis for reconstructing images that are spatially divided into distinct regions.

14. A system for tomographic imaging according to claim 12, wherein the first processing system is programmed with instructions for executing on the first processing system to control activation of capacitance plate segments using an evolution of a reconstructed image.

15. A system for tomographic imaging according to claim 12, wherein the first processing system is programmed with instructions for executing on the first processing system to control activation of capacitance plate segments to enhance resolution at specific regions in the imaging domain based on feedback data received from the measuring circuit.

16. A system for tomographic imaging according to claim 12, wherein the first processing system is programmed with instructions for executing on the first processing system to use singular value decomposition analysis to identify different categories of capacitance data and relate them to distinct regions in an imaging domain of the sensor.

\* \* \* \* \*